United States Patent [19]
Olech et al.

[11] Patent Number: 6,156,182
[45] Date of Patent: Dec. 5, 2000

[54] ENCAPSULATED IPG STRIPS

[75] Inventors: Lee Olech, Rodeo; Adriana J. Harbers, Martinez, both of Calif.

[73] Assignee: Bio-Rad Laboratories, Inc., Hercules, Calif.

[21] Appl. No.: 09/195,983

[22] Filed: Nov. 19, 1998

[51] Int. Cl.⁷ .................................................. G01N 27/26
[52] U.S. Cl. ............................................ 204/610; 204/616
[58] Field of Search ..................................... 204/456, 459, 204/606, 610, 641, 644, 616; 435/4; 436/515, 516

[56] References Cited

U.S. PATENT DOCUMENTS

| 3,888,758 | 6/1975 | Sheik Saeed | 204/613 |
| 4,443,319 | 4/1984 | Chait et al. | 204/616 |
| 5,209,831 | 5/1993 | MacConnell | 204/616 |
| 5,773,645 | 6/1998 | Hochstrasser | 204/456 |
| 5,989,400 | 11/1999 | Islam | 204/466 |

FOREIGN PATENT DOCUMENTS

| 2908044 | 8/1979 | Germany . |
| 363302352 | 12/1988 | Japan . |
| WO 93/13410 | 7/1993 | WIPO . |
| WO 96/13717 | 5/1996 | WIPO . |
| WO 96/34276 | 10/1996 | WIPO . |
| WO 98/57161 | 12/1998 | WIPO . |
| WO 98/59092 | 12/1998 | WIPO . |
| WO 99/33550 | 7/1999 | WIPO . |

OTHER PUBLICATIONS

JPAB abstract of Tsuyoshi et al. JP 363302352 A, Dec. 1988.
DWPI abstract of Bauer et al. DE 2908044 A, Aug. 1979.

*Primary Examiner*—Arlen Soderquist
*Assistant Examiner*—Alex Noguerola
*Attorney, Agent, or Firm*—Townsend and Townsend and Crew LLP

[57] ABSTRACT

Immobilized pH gradient (IPG) strips are encapsulated in an enclosure that seals the strip from atmospheric exposure and yet contains sufficient volumetric capacity to accommodate the strip in rehydrated form. The enclosure contains a pair of electrode access apertures each of which is spanned by a dialysis membrane to permit electrical contact between external electrodes and the encapsulated IPG strip, and one or more sample application apertures through which liquid sample can be applied to the strip. Each of the apertures is covered by a protective cover or flap that is removable to expose the aperture.

4 Claims, 3 Drawing Sheets

ENCAPSULATED IPG STRIPS

BACKGROUND OF THE INVENTION

Electrophoretic separations as a means of purifying proteins and separation complex protein mixtures have assumed many different forms. The separations vary in the composition of separation medium, the geometrical configuration of the medium, the manner in which mobility through the medium is achieved, and the parameter on which separation is based. One type of electrophoretic separation which is particularly useful for protein separations is a separation performed in a linear separation medium whose pH varies with the distance along the medium. A prominent example of a separation process that utilizes this type of medium is isoelectric focusing, a process by which proteins or other amphoteric substances migrate under the influence of an electric field along the pH gradient, each species continuing its migration until it reaches a location at which the pH in the medium and the isoelectric point of the species are equal. When this condition is achieved, the net charge on the species and hence the driving force for migration are zero, and migration ceases. By the completion of the procedure, the various species in a sample occupy positions in discrete, non-moving ("isoelectrically focused") zones along the pH gradient that correspond to their isoelectric points.

Isoelectric focusing may constitute the entire separation process, in which case the components of the sample mixture are identified by the location of the zones (in comparison to a standard) and the amount of each component is determined by the relative intensity of its zone as detected by standard detection methods. Isoelectric focusing can also serve as the first dimension of a two-dimensional separation, the second dimension being performed by placing the linear medium with its isoelectrically focused zones along one edge of a two-dimensional (slab-shaped) separation medium, preferably one that does not contain a pH gradient or one in which separation is performed by way of a separation parameter other than the isoelectric point of the species. An electric field is then imposed in a direction transverse to the linear medium, causing migration of the contents of each focused zone out of that medium and into the slab-shaped medium along parallel paths, the contents of each zone thereby undergoing further separation.

The most convenient means of achieving and maintaining the pH gradient needed for isoelectric focusing is the use of a dimensionally stable medium consisting of a molecular matrix to which functional groups have been attached that are either charged or chargeable by the placement of the medium in an electric field. Strips of solid material that contain such groups are commonly referred to as "immobilized pH gradient" ("IPG") strips. Examples of such strips and their composition and structure are described by Rosengren et al. in U.S. Pat. No. 4,130,470, issued Dec. 19, 1978. The solid material that forms the matrix of the strip is either a granular, fibrous, or membrane material, or a gel. Examples of suitable materials are polyacrylamide, cellulose, agarose, dextran, polyvinylalcohol, starch, silica gel, and polymers of styrene divinyl benzene, as well as combinations of these materials. Examples of positively charged or chargeable groups are amino groups and other nitrogen-containing groups. Examples of negatively charged or chargeable groups are carboxylic acid groups, sulfonic acid groups, boronic acid groups, phosphonic or phosphoric acid groups, and esters of these acids. The groups are immobilized on the matrix by covalent bonding or by any other means that will secure the positions of the groups and prevent their migration when exposed to an electric field or to the movement of fluids or solutes through the strip. When the matrix is a polymer, for example, a typical means of immobilization, is the inclusion of charged monomers to copolymerize with the uncharged monomers that form the bulk of the polymer or the inclusion of charged crosslinking agents. Copolymerization or crosslinking can be performed in a manner that will result in a monotonic increase or decrease in the concentration of the charged or chargeable groups, thereby producing the gradient. Although IPG strips are formed in hydrated condition, they are typically dehydrated once formed and are supplied to users in this condition. Rehydration for use is conveniently achieved by the sample itself, which is applied to the strip and the strip permitted to stand for a sufficient period of time to achieve full rehydration.

While IPG strips offer the advantage of a stable and well-controlled pH gradient and require only rehydration to be ready for use, their use poses certain difficulties. Once a strip is rehydrated, for example, care must be taken to assure that the strip does not suffer dehydration during use by losing water to the atmosphere. Since the strip is generally not contained in a capillary or length of tubing or other enclosure that would shield it from atmospheric exposure, dehydration is typically prevented by covering the strip with an electrically insulating, water-immiscible liquid such as mineral oil, and keeping the strip covered during isoelectric focusing. Furthermore, contact of the two ends of the strip with electrodes must be made and maintained through the mineral oil. In addition, once isoelectric focusing has been performed, the mineral oil must be completely removed from the strip before the strip can be used in a second dimension separation, since residual mineral oil will interfere with the electrical continuity between the strip and the slab gel.

SUMMARY OF THE INVENTION

An encapsulated IPG strip has now been devised that overcomes the disadvantages noted above. The IPG strip in dehydrated form is sealed in an elongated enclosure that has sufficient volumetric capacity to accommodate the dimensions of the strip after rehydration. The enclosure is substantially fluid- and vapor-impermeable except for two sets of apertures, one set to permit electrical contact through the enclosure walls between the retained strip and the two electrodes used in the electrophoretic separation (the electrodes being part of the electrophoresis cell in which the encapsulated IPG strip will be placed), and the other for the application of a liquid to the strip for purposes of both rehydrating the strip and applying a liquid sample to the strip. The first set, referred to herein for convenience as "electrode access apertures," consists of two apertures, one at or near each end of the enclosure. The second set, referred to herein for convenience as "sample application aperture(s)," consists of at least one, and often only one, aperture located preferably toward the center of the enclosure, most conveniently midway between the two electrode access apertures. The electrode access apertures are not open, each instead being spanned by a barrier that is ion-permeable to permit electrical continuity across the aperture yet protein-impermeable to prevent loss of sample constituents. The sample application aperture is not spanned by such a barrier, instead being fully open to provide a means for inserting the entire sample into the enclosure. All apertures are covered by removable protective closures to preserve the contents and protect the enclosure and the IPG strip from damage during shipment, storage, and use.

These and other features, advantages and embodiments of the invention will be apparent or more readily understood from the description that follows.

DETAILED DESCRIPTION OF THE INVENTION AND SPECIFIC EMBODIMENTS

While this invention is susceptible of a variety of shapes, configurations and arrangements, the drawings and the following description address one particular embodiment in detail as a means of facilitating an understanding of the invention as a whole.

Figure 1:
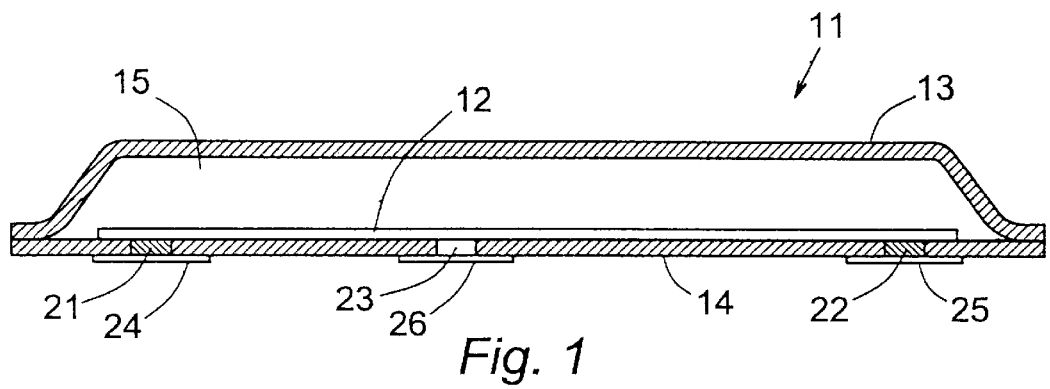
FIG. 1 is a side cross section of an encapsulated IPG strip in accordance with this invention, showing the IPG strip in dehydrated condition.
Figure 2:
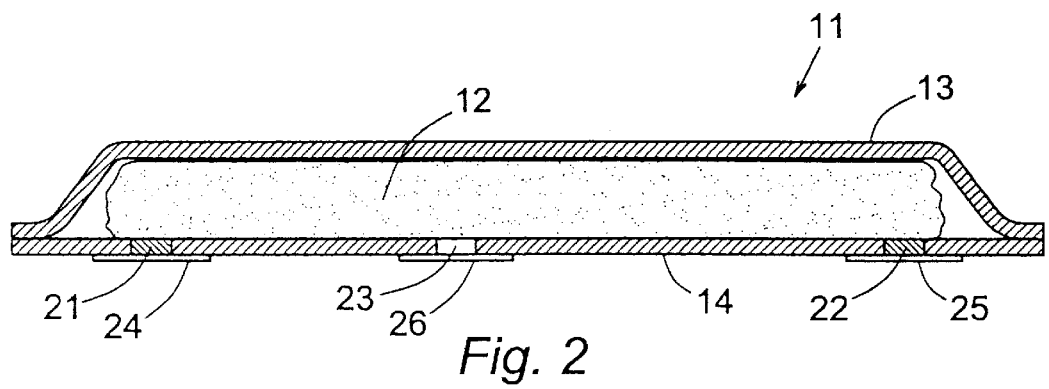
FIG. 2 is a view identical to that of FIG. 1 except that the IPG strip is shown in rehydrated condition.

FIGS. 1 and 2 are side cross sections of an encapsulated IPG strip 11, which includes an IPG strip 12 encapsulated inside an enclosure that consists of two plates of inert, electrically insulating material that is at least substantially fluid-impermeable and vapor-impermeable, i.e., an upper plate 13 and a lower plate 14, bonded together along each of their four edges. The cross section shown in these drawings is taken parallel to the long sides, the enclosures being elongated rectangles roughly conforming in shape to the dimensions of the IPG strip. The lower plate 14 is flat, while the upper plate 13 is raised in the center relative to its periphery to form a chamber 15 to contain the IPG strip. The chamber is large enough to contain the IPG strip both in its dehydrated form, as shown in FIG. 1, and its rehydrated (water-swelled) form, as shown in FIG. 2.

The lower plate 14 contains three apertures 21, 22, 23. The two outermost apertures 21, 22 are electrode access apertures, and are positioned at locations near the two ends of the IPG strip. These apertures are not open passages, but are instead closed by barriers that are permeable to ions to permit the passage of an electric current, but impermeable to large molecules such as proteins and other types of solutes that are typically present in samples to be analyzed by electrophoretic separations. Dialysis membranes are well suited for use as the barrier material for these apertures. Dialysis membrane materials are well known in the art and readily available from industrial suppliers. Examples of such materials are regenerated celluloses such as cuprophan, cuprammonium cellulose, and saponified cellulose ester; synthetically modified celluloses such as hemophan, cellulose acetate, and celulose triascetate; and synthetics such as polysulfone, polycarbonate, polyamide, polyacrylonitrile, sulfonated polyacrylonitrile, polyvinyl alcohol, and poly (methyl methacrylate). The third aperture 23 is fully open to permit the application or insertion of the sample into the chamber. Each of the three apertures is covered by a removable fluid-impermeable barrier (i.e., a cover flap or strip) 24, 25, 26. The purposes of these removable barriers will be evident from the descriptions of FIGS. 5, 6, and 7 below.

Figure 3:
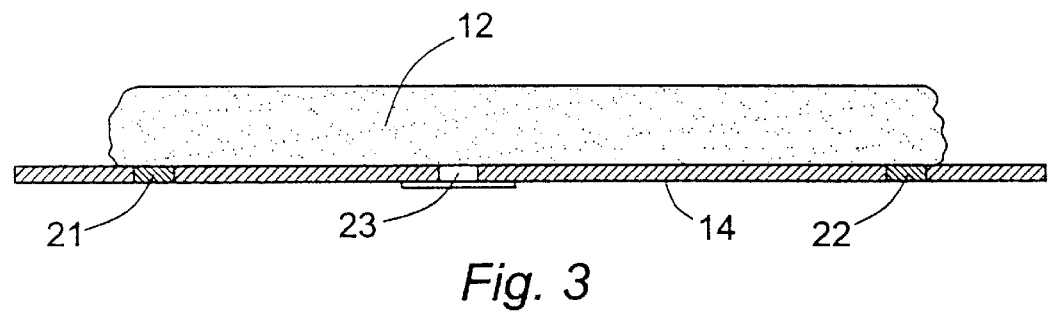
FIG. 3 is a view identical to that of FIG. 2 except that the upper plate of the enclosure has been removed to exposed the IPG strip.

The peripheral bond joining the upper plate 13 to the lower plate 14 is one that securely holds the two plates together and is fluid-impermeable to retain any fluids or vapors in the chamber 15. The bond is nevertheless one that is also readily breakable to permit the user to separate the two plates by manual force to expose the IPG strip after isoelectric focusing has been performed in the IPG strip. FIG. 3 depicts the lower plate 14 and IPG strip 12 after the bond has been broken and the upper plate 13 has been removed. The swelled IPG strip 12 with its isoelectrically focused zones can now be lifted from the lower plate 14 and placed in position in an appropriate electrophoresis cell for the second dimension of a two-dimensional separation.

Figure 4:
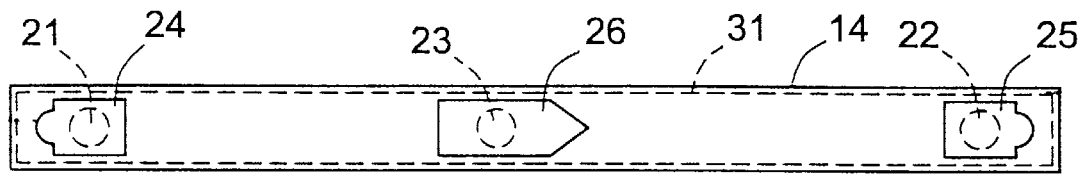
FIG. 4 is a plan view of the underside of the encapsulated IPG strip shown in the preceding Figures, prior to use.
Figure 5:
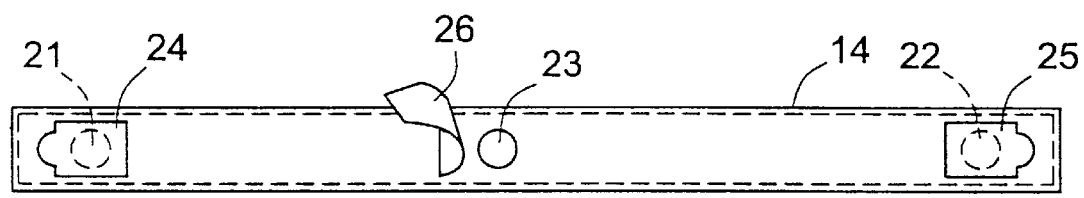
FIG. 5 is a view identical to that of FIG. 4, during application of the sample.
Figure 6:
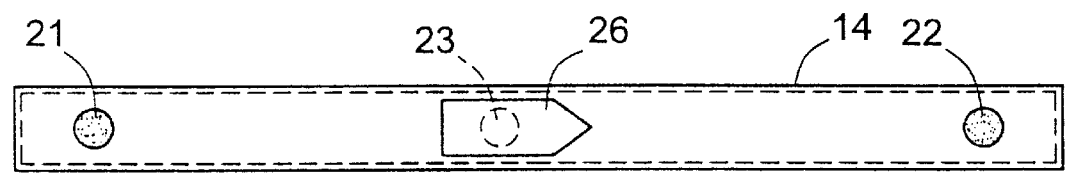
FIG. 6 is a view identical to that of FIGS. 4 and 5, except that the protective covers over two of the apertures have been removed to place the device in condition for isoelectric focusing.

FIGS. 4, 5, and 6 show the underside of the lower plate 14 of the enclosure of the preceding drawings in three stages of the use of the encapsulated IPG strip. The dashed line 31 indicates the location of the bonded peripheral area on the upper side of the lower plate. The three apertures 21, 22, and 23 are shown in each of the three Figures, covered by the protective covers in some cases and exposed in others.

FIG. 4 shows the device as it may be supplied to the user, prior to use. Each of the apertures is covered by its respective protective cover 24, 25, 26. The covers 24, 25 over the two electrode access apertures are coated on their contact surfaces with a suitable adhesive to form fluid-retaining barriers over the dialysis membranes to both protect the membranes from mechanical damage during shipping and handling, and to retain any fluids in the chamber during rehydration of the IPG strip, and yet to permit removal of the covers at the appropriate stage of the procedure. The cover 26 over the sample application aperture is likewise coated on its contact surface with a suitable adhesive that will prevent loss of fluids from the chamber.

FIG. 5 shows the device in condition for sample to be placed inside the chamber. The cover 26 over the sample application aperture is a flap that is turned back to expose the aperture and permit sample to be added through the aperture to fill the chamber. One edge 32 of the flap is permanently bonded to the lower plate 14 so that the flap will not be removed entirely and can be resealed over the aperture. The covers 24, 25 over the electrode access apertures are still in place where they serve to prevent loss of sample liquid from the chamber, either by liquid flow or evaporation. The apertures are not limited to any particular location on the device, and can be either on one plate as shown or distributed between both plates, and in any of various locations on the plates. The configuration shown in the drawings, however, is preferred for ease of use of the encapsulated strip in an electrophoresis cell.

Once the sample is applied and the IPG strip is fully rehydrated, the cover flap 26 over the sample application aperture 23 is returned to its original position, sealing the aperture, and the two covers 24, 25 over the electrode access apertures are removed entirely. This condition is shown in FIG. 6. The encapsulated IPG strip is now ready for isoelectric focusing, which is achieved by placement of the encapsulated strip in an electrophoresis cell such that the electrodes in the cell will be in contact with the outer surfaces of the dialysis membranes 21, 22.

Figure 7:
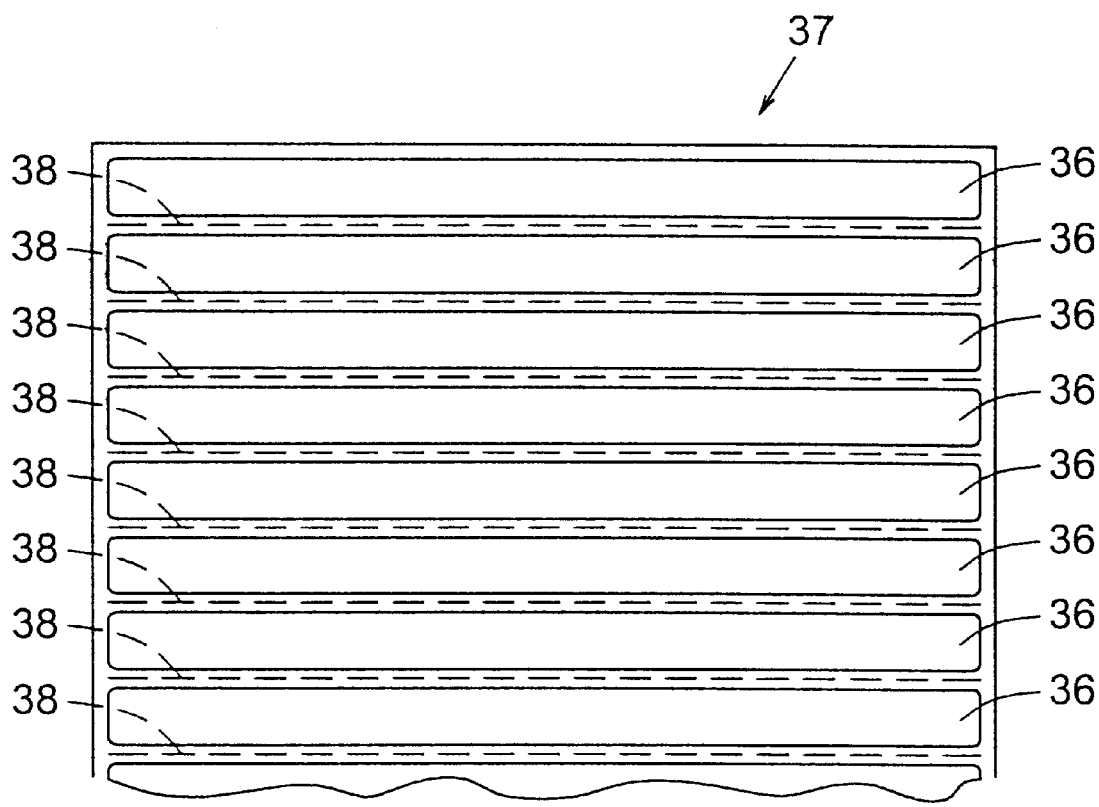
FIG. 7 is a top plan view of a sheet of encapsulated IPG strips joined together, each individual encapsulated strip being the same as those illustrated in the preceding Figures.

A particularly useful embodiment of the invention is shown in FIG. 7, which depicts a series of encapsulated IPG strips 36, each of which may be identical to those shown in the preceding Figures, joined together along their side edges to form a sheet 37. Samples can be applied to the individual encapsulated strips in the sheet and the entire sheet can be placed in an electrophoresis cell to run all strips simultaneously. Alternatively, individual encapsulated strips or groups of strips can be separated from the sheet along scored or otherwise readily separable lines, represented in the Figure by dashed lines 38.

The dimensions and materials of construction of the encapsulated strips of this invention are not critical to the invention and can vary. The typical IPG strip is approximately 3 mm in width and approximately 18 cm in length. In dehydrated form, the typical strip is less than 0.1 mm in thickness and has a backing of approximately 0.2 mm in thickness. The dimensions of the two plates forming the enclosure are preferably such that the chamber 15 has a volumetric capacity that is slightly larger than the volume of the rehydrated strip. The backing serves to secure the dimensional integrity of the strip material (the gel) and is generally fluid-impermeable and electrically insulating. In the embodiments shown in the drawings hereto, the strip, when placed in the enclosure during manufacture of the device, is positioned with the gel side facing the apertures. A typical hole size for the electrode access holes is about 2 mm to about 2.5 mm in diameter, while a typical hole size for the sample application hole is about 1.5 mm in diameter. The two parts of the enclosure may be made of rigid plastic or any kind of chemically inert, electrically insulating material. The two plates may be bonded together by conventional means, such as sonic welding or an adhesive. The materials used for the cover flaps may be any thin, flexible materials that retain moisture, and the releasable sealing character may be achieved by the use of a pressure-sensitive adhesive. The flap over the sample application aperture may be irremovably affixed to the lower plate along one edge by a cured adhesive or a sonic weld. A sheet containing multiple strips as shown in FIG. 7 may contain ten to twelve or more individual strips.

The foregoing description is offered primarily for purposes of illustration and is not intended to limit the scope of the invention. It will be readily apparent to those skilled in the art of electrophoresis and the use of IPG strips that further variations and modifications can be made without departing from the spirit and scope of the invention.

What is claimed is:

1. A device for use in isoelectric focusing, comprising:

an immobilized pH gradient strip;

an elongate enclosure enclosing said strip, said enclosure defined by first and second walls of fluid-impermeable material releasably joined together along their peripheries and shaped to form a chamber sized to contain said strip and to permit swelling of said strip upon wetting;

first and second apertures defined as electrode access apertures located on one side of said enclosure and spaced apart from each other, each said electrode access aperture spanned by a ion-permeable yet protein-impermeable membrane and covered with a removable vapor-impermeable barrier; and a third aperture, defined as a sample application aperture, in said enclosure, between said first and second apertures, covered with a removable and resealable vapor-impermeable barrier.

2. A device in accordance with claim 1 in which said removable vapor-impermeable barriers covering said electrode access apertures are adhered to the exterior of said enclosure by a pressure-sensitive adhesive.

3. A device in accordance with claim 1 in which said removable vapor-impermeable barrier covering said sample application aperture is adhered to the exterior of said enclosure by a pressure-sensitive adhesive.

4. A device in accordance with claim 1 in which said removable and resealable vapor-impermeable barrier covering said sample application aperture is a flap of material one end of which is irremovably affixed to said enclosure.

* * * * *